United States Patent
Allen et al.

[11] Patent Number: 6,039,868
[45] Date of Patent: Mar. 21, 2000

[54] BLOOD SEPARATOR SYSTEM

[75] Inventors: Michael P. Allen, Los Altos; Stoughton L. Ellsworth, Palo Alto; Lawrence M. Ensler, Los Altos; Kumar Subramanian, Pleasanton, all of Calif.

[73] Assignee: First Medical, Inc., Mountain View, Calif.

[21] Appl. No.: 08/839,879

[22] Filed: Apr. 16, 1997

Related U.S. Application Data

[63] Continuation of application No. 08/386,242, Feb. 9, 1995, abandoned.

[51] Int. Cl.⁷ .................................................. B01D 36/00
[52] U.S. Cl. ........................... 210/232; 210/258; 210/295; 417/477.1
[58] Field of Search .................................. 210/645, 650, 210/651, 767, 232, 233, 236, 252, 257.1, 258, 295, 416.1, 435, 446, 483, 488, 489, 492, 496; 422/100, 101, 102, 104; 436/177, 178; 417/477.1, 477.9, 477.11; 604/153, 411

[56] References Cited

U.S. PATENT DOCUMENTS

| | | | |
|---|---|---|---|
| 2,570,639 | 10/1951 | Cahan | 210/233 |
| 2,612,160 | 9/1952 | Barr | 210/233 |
| 3,663,374 | 5/1972 | Moyer et al. | 195/103.5 |
| 3,723,030 | 3/1973 | Gelfand | 417/477.3 |
| 3,737,251 | 6/1973 | Berman et al. | 417/477.3 |
| 3,784,323 | 1/1974 | Sausse | 604/153 |
| 3,814,258 | 6/1974 | Ayres | 210/359 |
| 3,927,955 | 12/1975 | Spinosa et al. | 417/477.11 |
| 4,086,060 | 4/1978 | Hermann, Jr. | 23/259 |
| 4,201,406 | 5/1980 | Dennehey et al. | 604/411 |
| 4,210,138 | 7/1980 | Jess et al. | 417/477.11 |
| 4,233,001 | 11/1980 | Schmid | 417/475 |
| 4,278,085 | 7/1981 | Shim | 417/477.11 |
| 4,477,575 | 10/1984 | Vogel et al. | 436/170 |
| 4,552,516 | 11/1985 | Stanley | 417/477.11 |
| 4,599,055 | 7/1986 | Dykstra | 417/477.11 |
| 4,605,503 | 8/1986 | Bilstad et al. | 210/651 |
| 4,678,757 | 7/1987 | Rapkin et al. | 436/169 |
| 4,680,025 | 7/1987 | Kruger et al. | 604/6 |
| 4,753,776 | 6/1988 | Hillman et al. | 422/101 |
| 4,816,224 | 3/1989 | Vogel et al. | 422/55 |
| 4,828,716 | 5/1989 | McEwen et al. | 210/740 |
| 4,888,115 | 12/1989 | Marinaccio et al. | 210/651 |
| 4,933,092 | 6/1990 | Aunet et al. | 436/169 |
| 4,952,516 | 8/1990 | Matkovich | 436/170 |
| 4,957,637 | 9/1990 | Cornell | 210/782 |
| 4,970,052 | 11/1990 | Oberhardt et al. | 422/101 |
| 4,980,297 | 12/1990 | Haynes et al. | 436/178 |
| 4,987,085 | 1/1991 | Allen et al. | 436/169 |
| 4,999,163 | 3/1991 | Lennon et al. | 422/58 |
| 5,000,922 | 3/1991 | Turpen | 422/101 |
| 5,110,724 | 5/1992 | Hewett | 435/11 |
| 5,132,086 | 7/1992 | Allen et al. | 422/56 |
| 5,133,650 | 7/1992 | Sunderland et al. | 417/477.2 |
| 5,135,719 | 8/1992 | Hillman et al. | 422/101 |
| 5,151,184 | 9/1992 | Ferkany | 210/514 |
| 5,186,843 | 2/1993 | Baumgardner et al. | 210/767 |
| 5,195,992 | 3/1993 | Dudar et al. | 604/411 |
| 5,213,483 | 5/1993 | Flaherty et al. | 417/477.2 |
| 5,234,608 | 8/1993 | Duff | 210/806 |
| 5,262,049 | 11/1993 | Ferkany | 210/258 |
| 5,262,067 | 11/1993 | Wilk et al. | 210/767 |
| 5,266,219 | 11/1993 | Pall et al. | 210/767 |
| 5,275,731 | 1/1994 | Jahn | 210/518 |
| 5,298,016 | 3/1994 | Gordon | 604/6 |
| 5,308,483 | 5/1994 | Sklar et al. | 210/232 |
| 5,484,239 | 1/1996 | Chapman et al. | 417/477.8 |

FOREIGN PATENT DOCUMENTS 2076068  11/1981  United Kingdom.

*Primary Examiner*—John Kim
*Attorney, Agent, or Firm*—Townsend and Townsend and Crew LLP

[57] ABSTRACT

A system for separating plasma from whole blood comprises a blood separation device and a blood separation driver. The blood separation device includes a flexible tube having a needle and shield at one end and a filter member at the other end. The needle may be used to access blood in a conventional blood collection device. The separation driver applies a peristaltic force to the flexible tube of the blood separation device, thus drawing blood from the collection device through the tube and to the filter member. Plasma may be collected from the filter element.

2 Claims, 5 Drawing Sheets

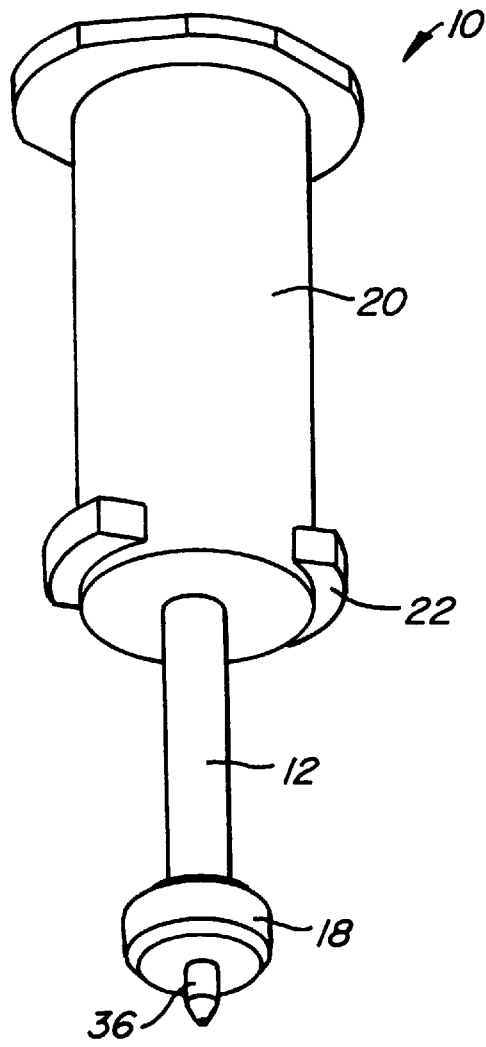
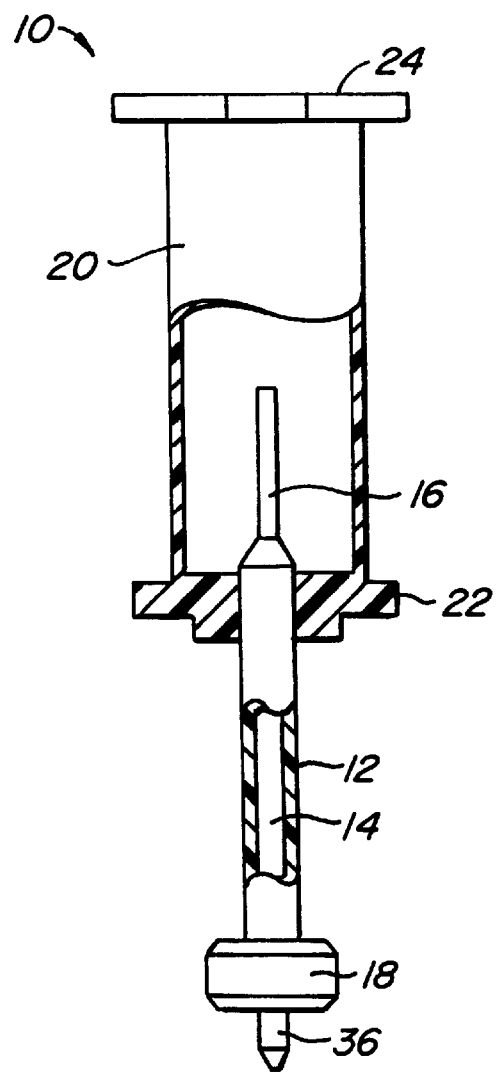
FIG. 1.
FIG. 2.

BLOOD SEPARATOR SYSTEM

This is a continuation of application Ser. No. 08/386,242, filed Feb. 9, 1995 now abandoned, the disclosure incorporated by reference.

BACKGROUND OF THE INVENTION

1. Field of the Invention

The present invention relates generally to systems and methods for assaying biological samples. More particularly, the present invention relates to a system and method for separating plasma from whole blood and transferring the plasma to an analytical substrate or device.

Many diagnostic markers and other analytes are best determined from patient blood samples. The ability to measure such markers and analytes directly in blood, however, is problematic because of the presence of blood cells, particularly red blood cells, in whole blood. Thus, a majority of analytical systems and methods intended for measuring blood markers and analytes rely on detection in a plasma or serum sample, not in a whole blood sample.

A wide variety of blood separation systems and methods have been developed over the years particularly for use in performing plasma and serum assays. Such systems may be generally categorized as centrifugal, chemical, and filtration. Centrifugal systems rely on centrifugation to remove cellular components from the blood. Chemical systems rely on antibodies, lectins, or the like, for binding and removing cellular components. Finally, filtration relies on chromatographic and/or size-exclusion filtration elements for separating the cellular blood components from the resulting plasma fraction.

The present invention is concerned in particular with filtration systems and methods for producing plasma from whole blood prior to performing an assay on the plasma. Heretofore, filtration elements have often been constructed integrally in assay devices, where blood is applied to the filter element and plasma is separated and flows to a reaction zone. Such systems, however, generally require that the whole blood be initially transferred from the standard blood collection device, such as a syringe or more commonly a vacuum collection tube, often using a transfer pipette. The need to use a transfer pipette is disadvantageous in several respects. It increases the assay procedure time and introduces a source of contamination and error. Equally important, the need to remove blood from the collection device in an intermediate transfer step increases the likelihood of that personnel performing the assay will be exposed to the blood.

For these reasons, it would be desirable to provide improved systems and methods for separating plasma from whole blood for use in plasma assays and assay devices. It would be particularly desirable if such systems and methods could eliminate the need to employ an intermediate transfer step between the blood collection device and the blood filtration device, such as the use of a transfer pipette. It would be particularly desirable if the methods and devices would permit the direct separation of plasma from blood in a totally closed system, including the blood collection device, which could be disposed of after use without release of blood or blood components from the closed system (other than the plasma which has been intentionally transferred to an assay system). Such methods and systems should further provide for accurate and precise (repeatable) measurement of the plasma being separated, as well as for direct transfer of the plasma to a test substrate, receptacle, or other assay system.

2. Description of the Background Art

U.S. Pat. No. 4,086,060, describes a blood filtering device which is employed between a blood collection device and a plasma receptacle. U.S. Pat. Nos. 4,980,297 and 4,970,052, describe plasma transfer devices which include needles for accessing blood collection devices and the rubber stoppers on the collection devices. The following patents describe other plasma separation systems and devices: U.S. Pat. Nos. 5,275,731; 5,262,049; 5,151,184; 4,957,637; 4,828,716; and 3,814,258. Filter elements for separating plasma from whole blood in combination with absorptive pads are shown in a number of patents, including U.S. Pat. Nos. 5,262,067; 5,132,086; 5,110,724; 4,987,085; 4,933,092; 4,816,224; 4,753,776; 4,477,575; and 3,663,374. Other patents showing assay devices including separation membranes and absorptive pads include U.S. Pat. Nos. 4,678,757; 4,952,516; 4,999,163; 5,000,922; 5,135,719; 5,186,843; 5,266,219; and 5,308,483.

SUMMARY OF THE INVENTION

According to the present invention, systems and methods are provided for separating plasma from whole blood and transferring the separated plasma to an analytical device or substrate. The system includes both a blood separation device and a blood separation driver. The blood separation device is connected directly to a conventional blood collection device, such as a vacuum collection device, and provides a fluid flow path and filter for separating plasma from blood in the collection device. The blood separation driver acts on the blood separation device to induce blood flow through the filter and plasma flow from an exit port in the separation device. A particular advantage of the present invention is that the assembly of the blood separation device and the blood collection device is entirely closed, except for the plasma exit port. Thus, all blood and blood components other than the transferred plasma remain contained and confined within the combination of the blood separation device and collection device which may be disposed of after the separation procedure in order to reduce the risk of exposing the operating personnel to the blood. Moreover, the risk of contamination is reduced since the blood driver is not exposed directly to the blood which remains contained within the combination of blood collection and separation devices.

In a first aspect, the method of the present invention comprises introducing whole blood into an inlet end of a flexible tube. By applying a peristaltic force to an external surface of the tube, blood flow through an internal lumen is induced from the inlet end to an outlet end. Blood flow from the outlet end is directed through a filter member, resulting in separation of cellular components and the production of plasma. Preferably, the peristaltic force is applied by removably inserting the flexible tube into a driver assembly and rotating a drive wheel in the assembly to apply the peristaltic force. After a preselected volume of plasma has been produced, the flexible tube and filter member can be removed from the driver and disposed of.

In a second aspect, the method of the present invention comprises connecting an inlet end of a flexible tube to a blood receptacle, such as a blood collection device. The flexible tube is placed in a driver assembly, and a drive wheel in the driver assembly is rotated to apply peristaltic force to an exterior surface of the tube, thus causing blood flow from the receptacle through an internal lumen in the tube, and outward through a filter member to separate cellular components and produce plasma. In a preferred aspect, the flexible tube is connected to the receptacle by piercing a needle at an inlet end of the tube through a septum or stopper in the receptacle, e.g., a conventional blood collection device. The tube is typically placed in the driver by releasably clamping the tube in a vertical orientation where an intermediate portion of the tube is exposed to the drive wheel. After a desired volume of plasma has been produced, the assembly of the tube, filter member, and blood receptacle can be removed from the driver and disposed of. A second flexible tube assembly may then be connected to a second receptacle, and the resulting assembly placed in the same driver in order to achieve plasma separation. Advantageously, the driver assembly is never exposed to whole blood or blood components.

A preferred blood separation device comprises a flexible tube having an inlet end, an outlet end, and a blood flow lumen therebetween. A needle structure is disposed at the inlet end of the flexible tube and a filter membrane is disposed at the outlet end of the flexible tube. The flexible tube provides a lumen to permit blood flow from the needle (which may be used to access a conventional blood collection device as described above) and to the filter member. The flexible tube may be inserted into a peristaltic or other driver assembly to induce the desired blood flow. Optionally, a receptacle shield may be attached to the inlet end of the flexible tube to surround the needle structure. The shield will be sized to receive a conventional blood collection device.

A blood separation driver according to the present invention comprises a frame, a clamp structure on the frame, and a peristaltic drive wheel on the frame. The clamp structure is disposed to removably secure a blood separation device, such as that described above. In an orientation which exposes the flexible tube to the peristaltic drive wheel, rotation of the drive wheel can thus induce blood flow from an inlet end to an outlet end of the flexible tube. Preferably, the driver comprises a collar for supporting the inlet end of the flexible tube in a vertical manner.

The present invention still further provides blood separator systems comprising both a blood separation device and a blood separation driver. The blood separation device includes a flexible tube, a needle structure at an inlet end of the flexible tube, and a filter member at the outlet end of the flexible tube. The blood separation driver includes a frame, a clamp for removably securing the blood separation device, and a peristaltic drive wheel which engages an exterior surface of the flexible tube to induce blood flow through the tubular lumen when it is secured in the clamp.

The preferred aspects of both the blood separation device and the blood separation driver are described above.

BRIEF DESCRIPTION OF THE DRAWINGS

FIG. 1 is a perspective view of a blood separation device constructed in accordance with the principles of the present invention.

FIG. 2 is an elevational view of the blood separation device of FIG. 1, shown with portions broken away.

DESCRIPTION OF THE SPECIFIC EMBODIMENTS

Figure 3:
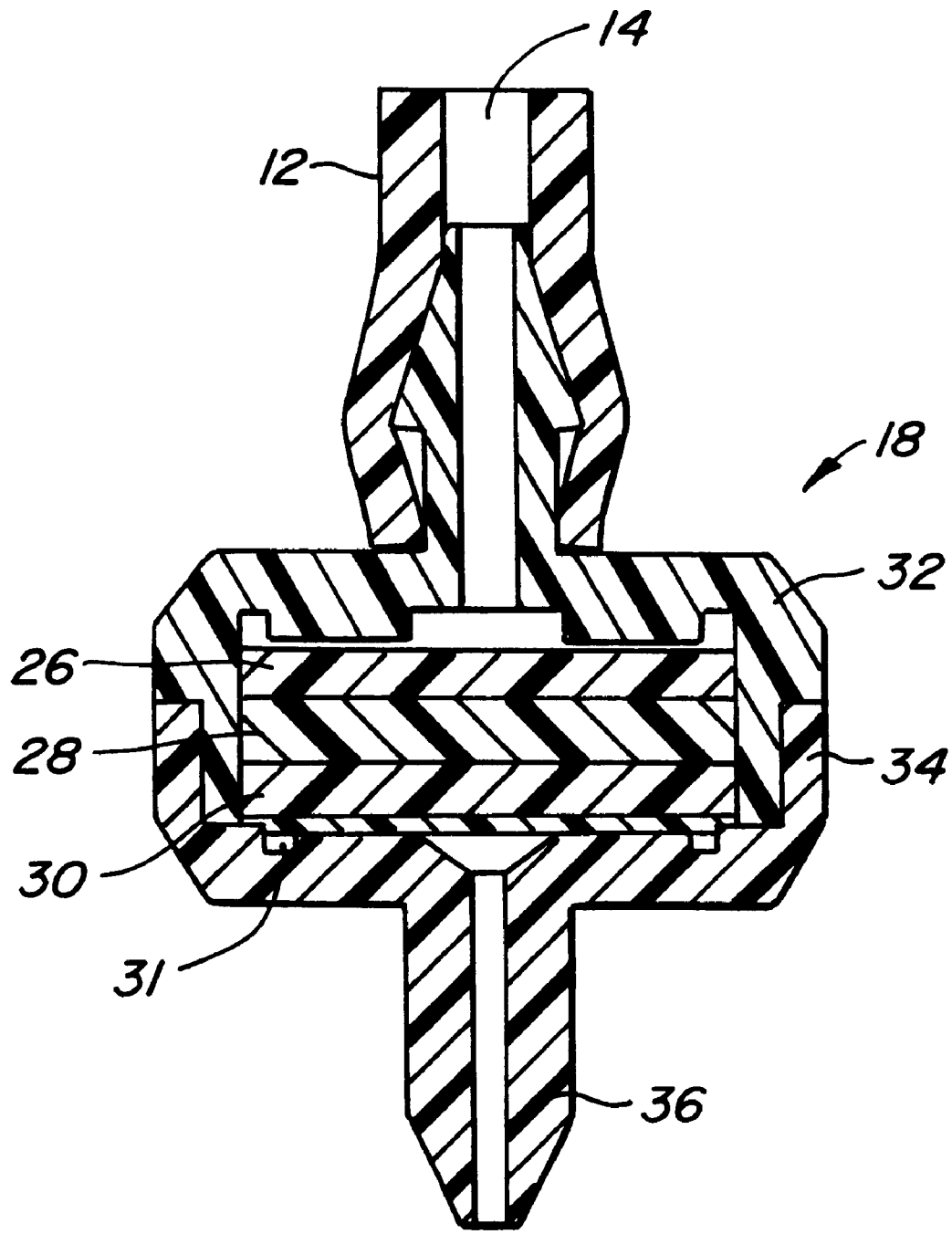
FIG. 3 is a detailed view of the filter element of the blood separation device of FIGS. 1 and 2, shown in section.
Figure 4:
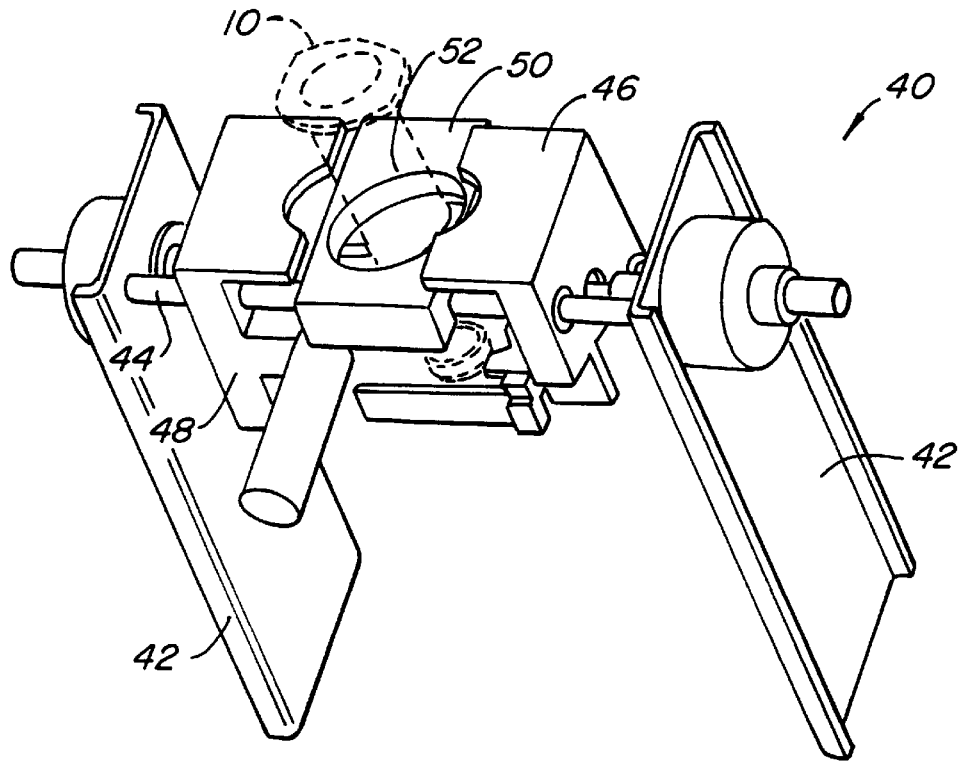
FIG. 4 is an isometric view of a blood separation driver constructed in accordance with the principles of the present invention.
Figure 5:
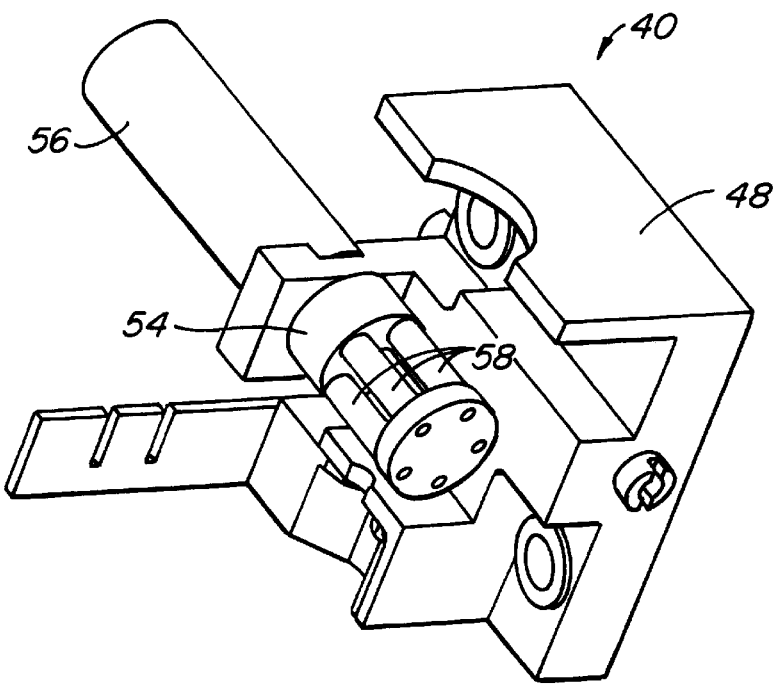
FIG. 5 is a detailed view of the peristaltic drive wheel and clamp element which form a part of the blood separation driver of FIG. 4.

The present invention comprises a system and method for providing plasma for subsequent analysis in order to qualitatively or quantitatively determine the presence of target markers, analytes, enzyme activities, proteins, small molecules, infectious organisms, drugs, and the like. Plasma consists of whole blood from which the blood cells, including both red blood cells and white blood cells, have been separated. Generally, blood proteins and other macromolecules, including the clotting proteins, immunoglobullins, and other blood factors and non-cellular components, remain in the plasma. In particular, the present invention provides for filtration of cellular components from whole blood to provide plasma as will be described in more detail hereinbelow. All blood components substantially smaller than the cellular components will remain in the separated plasma. Thus, virtually any test which can be performed on plasma can utilize plasma obtained by the systems and methods described below.

Separation of cellular components from whole blood according to the present invention will generally be obtained by two-stage filtration with a chromatographic filter element in series with a size-exclusion filter element. The chromatographic filter element will typically be a depth filter, often including two or more separate layers. The chromatographic filter element performs an initial separation of cellular components from the plasma based on chromatographic principles, i.e. the plasma will travel through the chromatographic element at a rate faster than the blood cells which, because of their size are preferentially slowed. The chromatographic filter element can be composed of any conventional filter medium, such as glass fiber, polyester fiber, plastic fiber, metal fiber, composite cellulose and synthetic fiber, nylon mesh, polyester mesh, synthetic fabric, and the like. A preferred chromatographic filter element material is glass fiber. The area and depth of the chromatographic filter element will depend on the volume of plasma to be separated from the applied whole blood, as described in more detail below. The chromatographic filter element will have a volume which is sufficiently large to retain blood cells and prevent blockage of the size-exclusion membrane so that a desired volume of plasma can pass through the combined filter member. Typically, the volume of the chromatographic filter element will be in the range from 25 mm$^3$, preferably from 25 mm$^3$ to 700 mm$^3$. The depth of the chromatographic filter element will typically be in the range from 1 mm to 10 mm, usually from 2 mm to 6 mm.

The size-exclusion filter membrane will have a pore size selected to exclude the passage of cells, typically being less than 7 $\mu$m, preferably being in the range from 0.1 $\mu$m to 7 $\mu$m, more preferably being from 0.4 $\mu$m to 3 $\mu$m. The size-exclusive membrane can be composed of any conventional membrane material, such as nitrocellulose, cellulose acetate, regenerated cellulose, polycarbonate, polyamide, and the like. A preferred size-exclusion filter membrane is polycarbonate.

In a preferred design, the size-exclusion membrane may be composed of or coated with a hydrophobic material, such as hydrophilic track-etched polycarbonate. A hydrophobic membrane surface will create a barrier which inhibits the passage of plasma unless a threshold positive pressure (referred to as the bubble point) is exceeded. Thus, the membrane can provide a valving effect where leakage of plasma is inhibited in the absence of pressure provided by the pump driver. This is a particular advantage in that the blood and plasma remaining in the blood separation device will remain contained to protect personnel from exposure to the blood and plasma before and after the separation is accomplished.

Materials and constructions for two-stage filter systems suitable for use in the present invention are described in U.S. Pat. No. 3,663,374, the full disclosure of which is incorporated herein by reference.

The filter members are provided as part of a blood separation device which includes a flexible tube having a needle or other access element at its inlet end and the filter (present in a filter member housing) at its outlet end. The flexible tube may be composed of any resilient material which is compatible with blood flow, particularly being non-thrombogenic and free from contaminants which might be released into the blood or plasma. Suitable materials include silicone rubber, latex, polyvinylchloride (PVC), Santoprene®, neoprene, and the like.

The dimensions of the flexible tube are not critical. For use with the blood separation driver described hereinafter, however, the tube will usually have a length in the range from about 10 mm to 100 mm, preferably from 20 mm to 50 mm. The tube will have an internal lumen for transporting blood having a diameter in the range from 0.5 mm to 5 mm, preferably from 1 mm to 3 mm. Typically, the external diameter of the tube will be from 1 mm to 7 mm, preferably from 1.5 mm to 5 mm. The tube will usually have uniform dimensions along its length, but such uniformity is not essential.

The access device will typically be a needle, hypotube, or other structure capable of piercing a rubber stopper or septum of the type found in conventional blood collection devices, such as vacuum collection devices, e.g. Vacutainers® available from Becton-Dickinson, Franklin Lakes, N.J. In particular, the needle structures will provide both for piercing of the septum and provide for an internal lumen to permit blood flow from the blood collection device into the flexible tube. Usually, but not necessarily, the lumen of the needle will be coaxially aligned with the lumen of the flexible tube. The filter member will be secured to the outlet end of the flexible tube and will further include an outlet port to permit outflow of separated plasma from the blood separation device. Optionally, a cylindrical shield is secured at the inlet end of the flexible tube and disposed about the needle or other access element. The shield has a length in the range from 20 mm to 75 mm and an internal diameter in the range from 15 mm to 30 mm and defines a receptacle for receiving and protecting the blood collection device when it is attached to the blood separation device. Optionally, the shield may be integral with the needle.

The blood separation driver can be any system capable of receiving and holding the blood separation device which can further induce blood flow through the device. In the broadest aspect of the present invention, the separation driver can induce blood flow by applying an external vacuum or internal pressurization within the assembly of the blood separation device and the blood collection device. It will be appreciated that internal pressurization within the blood collection device will cause outflow of blood through the blood separation device and the production of plasma. Alternatively, an external vacuum can draw blood flow from the blood collection device through the blood separation device. Internal pressurization and external vacuum, however, are generally less preferred since they increase the risk of loss of containment, particularly in the case of internal pressurization where the pressure source must be connected directly to the blood-containing collection device.

Preferred blood separation drivers according to the present invention will employ a mechanism for externally applying a peristaltic force to the flexible tube of the blood separation device described above. In the exemplary system, a peristaltic force is applied by a drive wheel having a plurality of rollers which contact and squeeze the flexible tube as the drive wheel is rotated. The successive and progressive squeezing of the tube results in positive displacement of blood through the tube.

Referring now to FIGS. 1–3, a blood separation device 10 comprises a flexible tube 12 having an internal lumen 14. A needle assembly 16 is attached at an inlet end of the tube 12 and a filter member 18 is attached at an outlet end of the tube. A shield 20 having a flange 22 at its base is disposed around the needle assembly 16 and attached to the inlet end of flexible tube 12. The shield 20 is opened at its upper end 24 so that it can receive a conventional blood collection device, such as a vacuum collection device, which can be introduced over the needle assembly 16, as described in more detail hereinafter.

The filter assembly 18 houses a three-layer filter element including individual glass fiber layers 26, 28, and 30 and final size exclusion membrane 31 below the glass fiber layers. The filter assembly 18 includes two separable halves 32 and 34 to facilitate assembly after the glass fiber layers 26, 28 and 30 and size exclusion membrane 31 have been introduced. A plasma outlet port 36 is provided at the base of the filter member 18 to permit directed transfer of the plasma to a desired assay device or substrate. Preferably, the size exclusion membrane is sealed tightly against the bottom glass fiber layer 30 to inhibit leakage of blood and plasma past the membrane.

Figure 6:
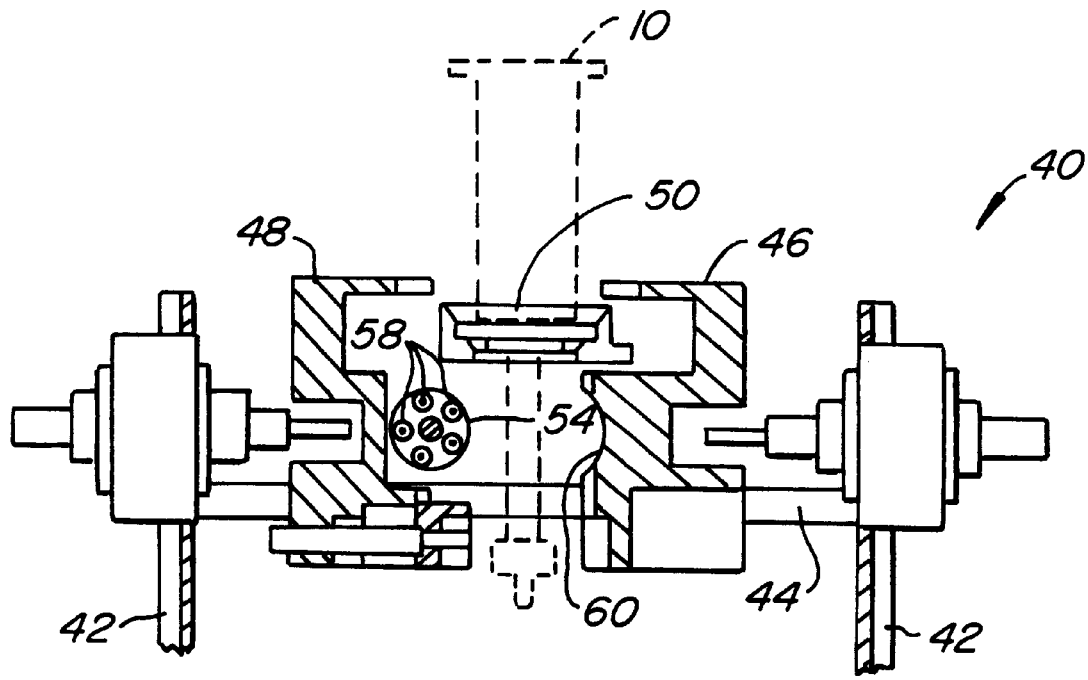
FIG. 6 is a detailed view of the opposed clamp elements and peristaltic drive element of the blood separation driver of FIG. 5, shown with the clamp elements in their open (spaced-apart) configuration.
Figure 7:
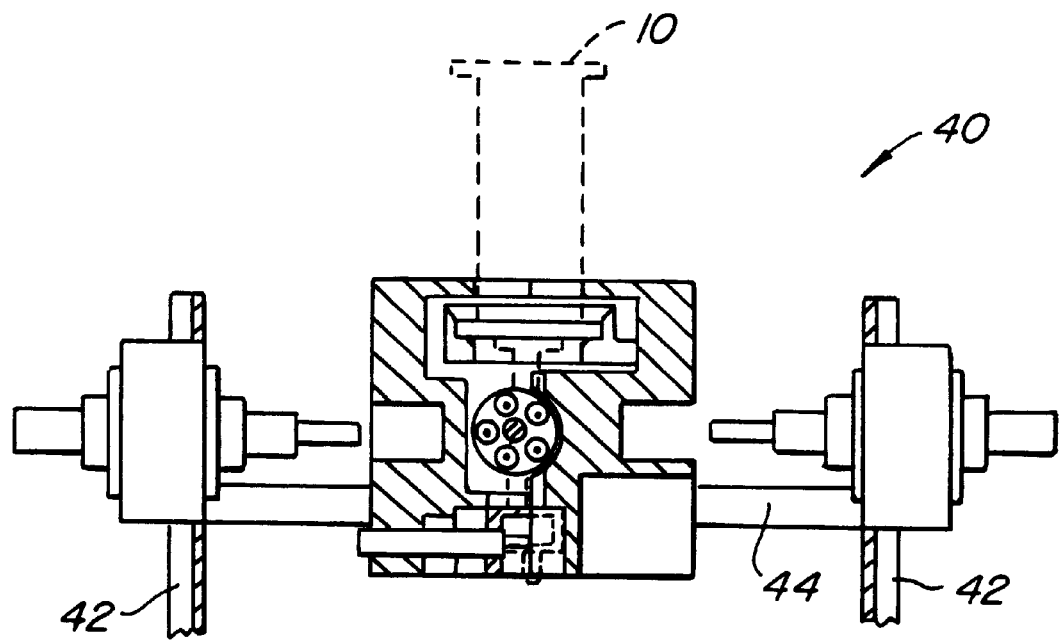
FIG. 7 is a view similar to FIG. 6, shown with the clamp elements in their closed configuration.
Figure 8:
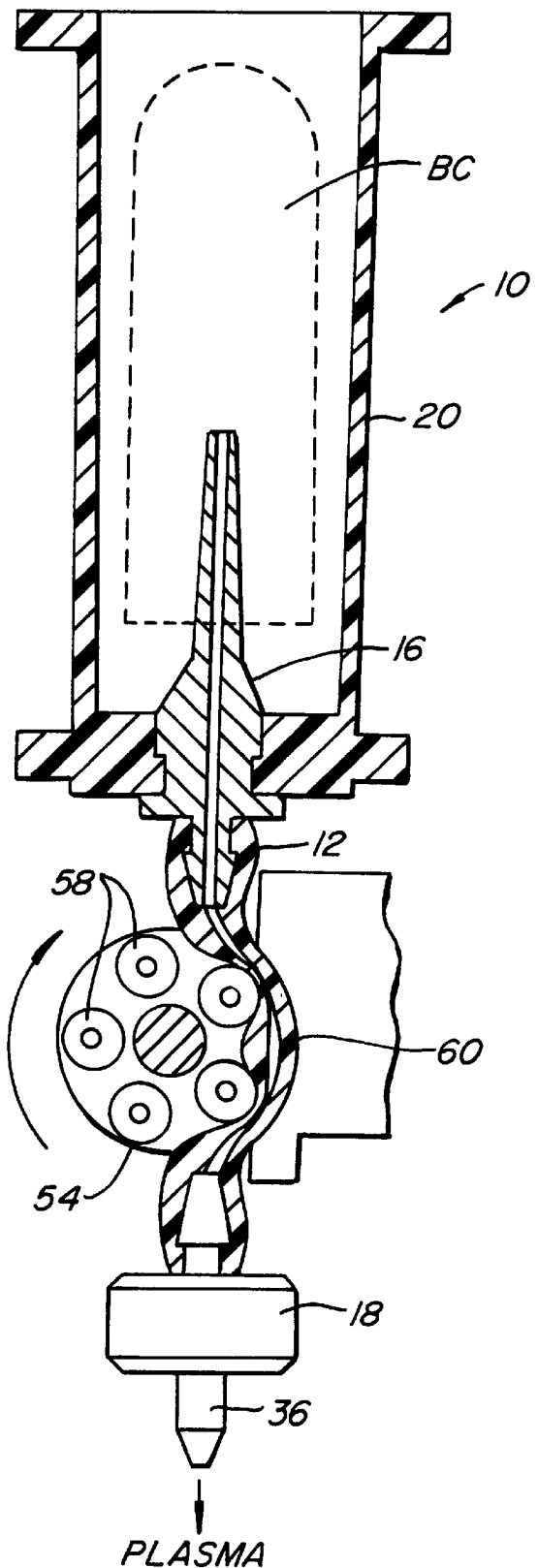
FIG. 8 is a detailed view of the peristaltic driver of the blood separation driver of FIG. 5, shown with a blood separation device in place.

The blood separation driver 40 is illustrated in FIGS. 4–7. The blood separation driver 40 includes frame members 42, support rods 44 extending between the frame members 42, and opposed clamp elements 46 and 48 which are mounted to translate relative to each other over the support rod 44. A support collar 50 is fixedly mounted on the support rods 44 and includes a central aperture 52 for removably receiving a blood separation device 10 of the type described above. A peristaltic drive wheel 54 is mounted on the clamp element 48, as best observed in FIG. 5. DC gear motor 56 is directly connected to the drive wheel 54 so that a plurality of rollers 58 on the drive wheel 54 can be incrementally turned relative to the clamp elements. As best observed in FIG. 6, an arcuate recess 60 is provided in the face of the opposed clamp element 46. When the opposed clamp elements 46 and 48 are brought together, as illustrated in FIG. 7, the rollers 58 of drive wheel 54 are received within the arcuate recess 60, leaving a narrow annular region therebetween for receiving the flexible tube 12 of the blood separation device 10, as best illustrated in FIG. 8.

The blood separation device 10 may be placed in the support collar 50 of the blood separation driver 40 when the opposed clamp elements 46 and 48 are spaced apart, as best observed in FIG. 6. After the blood separation device is properly positioned, the opposed clamp elements will be brought together and will capture the filter element in the lower portion thereof, as illustrated in FIG. 7. By anchoring the flexible tube 12 at both its inlet end (via the collar 50) and its outlet end (via capture of the filter member 18), the flexible tube will be held generally in place as it is captured between the rollers 58 of drive wheel 54 and the arcuate recess 60 of clamp 46. By then rotating the drive wheel 54, as illustrated by the arrow in FIG. 8, the peristaltic force draws blood from a blood collection device (BC) through the tube 12 with plasma flowing out from the port 36 of filter element 18. When a desired volume of blood plasma has been produced, rotation of the drive wheel 54 can be stopped, the opposed clamp elements 46 and 48 moved apart, and the assembly of the blood collection device (BC) and blood separation 10 removed from the driver. The assembly of the blood collection device (BC) and blood separation device 10 will be fully closed, except for the plasma outlet port 36. The presence of the size exclusion membrane 31, however, will inhibit loss of plasma from the port. Thus, the assembly can be disposed of as an integral unit, reducing the risk of exposure of the blood to personnel using an associated analytical system. Moreover, the analytical system itself will have the minimum exposure to blood and blood components.

Although the foregoing invention has been described in some detail by way of illustration and example, for purposes of clarity of understanding, it will be obvious that certain changes and modifications may be practiced within the scope of the appended claims.

What is claimed is:

1. A blood separator system comprising:
    a blood separation device including a flexible tube, a needle structure at an inlet end of the flexible tube, and a filter member at an outlet end of the flexible tube; and
    a blood separation driver including a frame, wherein the frame comprises a collar for supporting the inlet end of the flexible tube and one or more rods which extend laterally from the collar, a clamp for removably securing the blood separation device, wherein said clamp comprises first and second opposed clamping elements at least one of which is translatably mounted on the rods, a peristaltic drive wheel which is mounted on at least one of the clamping elements and engages an exterior surface of the flexible tube to pass blood through a lumen thereof when the tube is secured in the clamp, and at least one motor for translating one or both of the clamping elements to selectively secure and release the flexible tube when in place in the collar.

2. A blood separator system as in claim 1, wherein one of the clamping elements has an arcuate surface which is aligned with the drive wheel, wherein the flexible tube is captured between the drive wheel and the arcuate surface.

* * * * *